United States Patent [19]

Yasuda et al.

[11] 4,073,883
[45] Feb. 14, 1978

[54] METHOD FOR TREATMENT OF IMPAIRED HEARING

[75] Inventors: Koichi Yasuda; Yusuke Ikeda; Yukiaki Nishida, all of Fukuoka, Japan

[73] Assignee: Eisai Co., Ltd., Tokyo, Japan

[21] Appl. No.: 773,671

[22] Filed: Mar. 2, 1977

[30] Foreign Application Priority Data

Mar. 5, 1976 Japan ................... 51-23165

[51] Int. Cl.² ............ A61K 31/12; A61K 37/48
[52] U.S. Cl. .................. 424/94; 424/331
[58] Field of Search ............... 424/94, 331

[56] References Cited

U.S. PATENT DOCUMENTS

| | | | |
|---|---|---|---|
| 3,113,073 | 12/1963 | Grim | 424/94 |
| 3,317,381 | 5/1967 | Umehara | 424/94 |
| 3,426,125 | 2/1969 | Shigeta et al. | 424/94 |
| 3,534,137 | 10/1970 | Matsumura | 424/94 |

*Primary Examiner*—Stanley J. Friedman
*Attorney, Agent, or Firm*—Blanchard, Flynn, Thiel, Boutell & Tanis

[57] ABSTRACT

Impaired hearing is treated by administering to a human suffering from impaired hearing Coenzyme Q of the general formula:

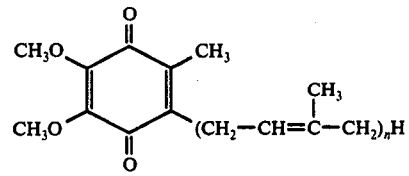

wherein $n$ is 7 to 10.

7 Claims, No Drawings

METHOD FOR TREATMENT OF IMPAIRED HEARING

BACKGROUND OF THE INVENTION

Field of the Invention

This invention relates to a method for the treatment of impaired hearing which comprises administering to a human suffering from impaired hearing a therapeutically effective amount of Coenzyme Q represented by the following general formula:

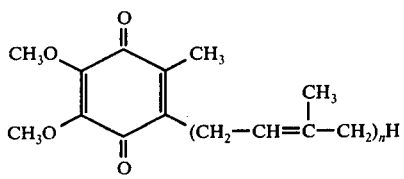

wherein $n$ represents an integer of 7 to 10.

DESCRIPTION OF THE PRIOR ART

Coenzyme Q is also called "ubiquinone".

Coenzymes Q were found in lipids of mitochondria in the hearts of oxen by Crane at the University of Wisconsin in 1957. Coenzymes Q having various numbers for $n$ in the above general formula are present in the natural world. Although the functions of the Coenzymes Q in vivo have not been known sufficiently, it is generally considered that they take part in the electron transport system in mitochondria. As for medical uses of Coenzymes Q, Coenzyme $Q_{10}$ is used at present as a medicament for treating congestive heart failure.

SUMMARY OF THE INVENTION

We have studied other medical indications of Coenzyme Q and have found, unexpectedly in view of the prior art, that Conenzymes Q are effective for the treatment of impaired hearing.

We have found that Coenzymes Q are, therefore, effective as medicaments for treating impaired hearing due to various causes such as continuous exposure to excessively loud noises, disease in the auditory pathways or in the auditory center, brain lesion, lesion of cortical brain substance, disease of the labyrinth, lesion of the auditory nerve or the central neural pathways, disease of blood vessels of the inner ear, and side effects of drugs.

Coenzyme Q can be continuously administered, because Coenzyme Q has a very low toxicity and does not exhibit side-effects in the treatment of impaired hearing.

An object of the present invention is to provide a method for the medical treatment of impaired hearing with Coenzymes Q.

Another object of the present invention is to provide a novel drug or a medically useful formulation containing Coenzymes Q which can be continuously administered without fear of significant side-effects for the treatment of impaired hearing.

Coenzymes Q used in the present invention, for example, Coenzyme $Q_{10}$ (the compound in which $n = 10$ in the above formula), can be mainly obtained synthetically, although it is possible to extract Coenzyme Q from animal organs. The physical and chemical properties of Coenzyme $Q_{10}$ produced synthetically are as follows.

(1) Properties

Coenzyme $Q_{10}$ is yellow or orange crystalline powder; easily soluble in chloroform, benzene and carbon tetrachloride; soluble in acetone and ether; insoluble in ethanol; and hardly soluble in water and methanol.

(2) Melting point

Approximately 48° C.

Further, the results of toxicity tests of Coenzyme $Q_{10}$ are as follows.

1. Acute toxicity test

In order to evaluate the acute toxicity of a single high dose administration of Coenzyme $Q_{10}$, male and female rats of Wistar strain and male and female mice of ICR-JCL strain were used, and oral, intramuscular, subcutaneous, and intravenous administrations were studied. For the oral administration of Coenzyme $Q_{10}$, gum Arabic suspension was used. For the intramuscular, subcutaneous and intravenous administrations, Coenzyme $Q_{10}$ was used as its solution in a nonionic surfactant, Nikkol HCO-60. Nikkol HCO-60 is a trade name of a non-ionic surfactant comprised of hydrogenated castor oil/polyoxyethylene-60 mole ether available from Nikko Chemicals, Co. Ltd., Japan.

Observations were carried out for 7 days by using six males and six females for each dose group. In any administration group, no change was recognized in the general condition, the body weight, the food intake, and the autopsy findings. As shown in the following Table 1, there was no case of deaths in rats and mice, at the maximum dose in each administration route.

Table 1

| Animal | Maximum dose (mg/Kg) by various routes | | | |
|---|---|---|---|---|
| | Route Oral | Intra-muscular | Subcu-taneous | Intravenous |
| Rats | 4000 | 500 | 500 | 250 |
| Mice | 4000 | 500 | 500 | 250 |

From the results described above, it can be concluded that the toxicity of Coenzyme $Q_{10}$ is extremely low and that $LD_{50}$ of Coenzyme $Q_{10}$ is far higher than the maximum dose mentioned above.

2. Subacute toxicity test (a) Subacute oral toxicity test in rats

Coenzyme $Q_{10}$ was compulsorily and orally administered every day for 5 weeks to each group consisting of 10 male rats and 10 female rats of Wistar strain. The dose was 40, 200, and 1000 mg/Kg/day, respectively. Coenzyme $Q_{10}$ was used in the form of gum Arabic suspension, while the solution containing gum Arabic alone was used as the control group. Collection of blood and urine samples and autopsies were carried out 5 weeks after the initiation of administration.

By comparing the administration group with the control group, there was shown no difference in connection with the general condition and the body weight of the animals during the period of administration. With respect to 4 dead animals during the experiment, the autopsies revealed that they had spontaneous pneumonia and aspiration pneumonia due to an error of administration.

No significant change was recognized from the hematological test and the biochemical test of blood and urine.

In the morphological observation, there was no significant change in the weight of each organ. Further, in the macroscopical and histological observation by hematoxylin. Eosine staining and liver fat staining, abnormality was not recognized.

As described above, there was not recognized the toxicity seemingly due to the administration of Coenzyme $Q_{10}$ in the subacute oral toxicity test carried out for 5 weeks.

(b) Subacute oral toxicity test in rabbits

Coenzyme $Q_{10}$ was compulsorily and orally administered every day for 23 days to each group consisting of 6 male rabbits and 5 female rabbits. The dose was 6, 60 and 600 mg/Kg/day, respectively. Coenzyme $Q_{10}$ was used in the form of gum Arabic suspension, whereas the solution containing gum Arabic alone was used as the control group. On the 24th day, blood samples were collected from all the animals, and 3 males and 2 females from each group were then selectively autopsied.

With reference to the general condition and the increase of body weight during the period of administration, there was shown no difference between the administration group and the control group. Abnormal findings were not obtained in the hematological test and the biochemical test of blood.

In the morphological observation, there was no effect on the weight of each organ. Further, abnormalities were not recognized in the macroscopical and histological observation by hematoxylin.Eosine staining and liver fat staining. Furthermore, in the electron-microscopic observation of liver carried out on the respective 7th, 14th, and 24th days after the administration, there were not recognized abnormal findings on the minute structure of the liver.

As mentioned above, there were not recognized the findings wherein the toxicity of Coenzyme $Q_{10}$ will be suggested in the subacute oral toxicity test carried out for 23 days. 3. Chronic oral toxicity test Coenzyme $Q_{10}$ was compulsorily and orally administered to each group consisting of 10 male rats and 10 female rats of Wistar strain for 26 consecutive weeks in a ratio of 6 days a week. The dose was 6, 60 and 600 mg/Kg/day, respectively. Coenzyme $Q_{10}$ was used in the form of gum Arabic suspension, whereas the solution containing gum Arabic alone is used as the control group. Collection of blood and urine samples and autopsies were carried out 26 weeks after the administration.

With respect to the general condition of the animals during the period of administration, there was shown no difference between the administration group and the control group, and the body weight in the administration group increased as same as that of the control group.

During the experiment, 11 males and 3 females died of spontaneous pneumonia and aspiration pneumonia due to an erroneous administration.

From the standpoint of hematological findings, the leukocytal percentages showed some increase and decrease, but do not provide the mutual relation depending upon the dose; the percentage being within the extent of physiological fluctuations.

No significant changes were recognized in the comparison of the administration group with the control group in the biochemical tests of blood and urine.

In the morphological observation, no significant increase and decrease in the weight of organs were shown. Further, abnormalities were not recognized in the macroscopical and histological observation by hemoxylin.Eosine staining and liver fat staining, when the administration group was compared with the control group.

As described above, no toxicity was observed in the chromic oral test of Coenzyme $Q_{10}$ carried out for 26 weeks.

4. Teratogenesis test

When the doses of 6, 60 and 600 mg/Kg/day of Coenzyme $Q_{10}$ were respectively administered to rats and mice, no adverse effects were noted in mothers, fetuses, and newborns.

As the results of the acute toxicity test, the subacute toxicity test, the chronic toxicity test, and the teratogenesis test, it was found that Coenzyme $Q_{10}$ used in the present invention was a very safe drug, without side-effects.

The effective amount of Coenzyme Q in accordance with this invention varies depending on types and symptoms of impaired hearing, and usually a daily dose of about 10–200 mg can be administered to the human patient.

Coenzyme Q can be administered in any form of powder, tablets, granules, capsules, injections, suppository, buccal drugs, and the like.

If Coenzyme Q is to be used in the form of powder, it can be adsorbed on an excipient such as magnesium carbonate, silicic acid anhydride (for example, available under trade names of Siloid and Cuplex), synthetic aluminum silicate, calcium phosphate and the like, or by an organic excipient such as lactose, corn starch, crystalline cellulose (for example, Avicel), glucose, hydroxypropyl cellulose, and the like.

If Coenzyme Q is to be used in the form of tablets and capsules, the above-mentioned Coenzyme Q powder can be manufactured into tablets or capsules in a conventional manner.

If Coenzyme Q is to be used in the form of an injectable liquid, it can be solubilized in water with a nonionic surfactant in accordance with any conventional method. As the nonionic surfactants, there may be mentioned hydrogenated castor oil/ethylene oxide addition products (for example, Nikkol HCO, a trademark and Emalex HC, a trademark), sorbitan fatty acid ester-/ethylene oxide addition products (for example, Tween, a trademark), alkylphenol/ethylene oxide addition products, fatty acid/ethylene oxide addition products, and sorbitan fatty acid esters (for example, Span, a trademark).

When Coenzyme Q is used in the form of an injectable liquid, it can be mixed with the usual additives such as propylene glycol and glucose.

The effect of the present invention by the use of Coenzyme $Q_{10}$ to treat impaired hearing will be shown with reference to the following clinical data.

CLINICAL TEST ON THE ADMINISTRATION OF COENZYME $Q_{10}$ FOR IMPAIRED HEARING (1) Method and period of administration 30 Mg/day of Coenzyme $Q_{10}$ was administered perorally three times a day after meal. Duration of administration differed with patients in the range of from two weeks to four months.

(2) Cases

Coenzyme $Q_{10}$ was administered to 9 patients having impaired hearing caused by administration of a drug (an antibiotic called poison against hearing organs). 8 of 9 patients were being administered with some poison against hearing organs at the time of the first medical examination of otorhinology. The remaining one patient was given streptomycin more than 10 years before then. It was pointed out that labyrinthine disorder was observed already and the administration of the poisons against hearing organs was discontinued in 5 of the 8 cases. In the remaining 3 cases, the treatment of the diseases with the poisons against hearing organs was continued with administration of Coenzyme $Q_{10}$.

In many cases, a combination of drugs such as combination of streptomycin (SM) with kanamycin (KM), kanendomycin (KDM) or gentamycin (GM) had been used.

There were used a glycyrrhizin preparation, a horse chestnut seed extract preparation and a vitamin B complex together with Coemzyme $Q_{10}$ mainly for improving combined symptoms in the vestibule and it is considered that the additives hardly exhibit effects of improving the hearing acuity.

(3) Method of judgement

Determination of hearing acuity threshold value in air conduction and bone conduction and recruitment test were effected using an audiometer in a sound-proof chamber.

The sum of the air conduction threshold value was determined in terms of decibel units and the values before and after the administration of Coenzyme $Q_{10}$ were compared with each other.

Air condition region values at 125 Hz, 250 Hz, 1 KHz, 2 KHz, 4 KHz and 8 KHz in audiogram were added together to obtain a value called the total region value at that time. In case the difference in the value between before and after the administration of Coenzyme $Q_{10}$ is more than ± 35 db, it was judged to be improved or worsened and in case the difference is within 35 db, it was judged to be unchanged. In case a threshold value of a certain frequency is scaled out, a value of the maximum output at that frequency plus 5 db. was employed.

(4) Control

For discussing the results in cases wherein Coenzyme $Q_{10}$ was not administered in the same manner as above, 4 patients of impaired hearing caused by a drug were picked out from cards. Therapeutical histories of the 4 patients were elucidated. Three of the four patients were being administered with streptomycin at the time of the first medical examination of otorhinology. After they were diagnosed as having impaired hearing caused by the drug, the administration of streptomycin was discontinued in 2 cases but the administration was continued in one case. One of the four patients was given streptomycin 14 years before then but was not given the same since then.

The patients excluding one patient were administered with an ATP preparation, Betahistine preparation, Isoxsuprine preparation or the like. Symptoms in the four cases were judged in the same manner as above.

(5) Results

The results of the treatment with Coenzyme $Q_{10}$ are shown in Table I and results of the treatment without Coenzyme $Q_{10}$ are shown in Table II. As shown in Table I, with Coenzyme $Q_{10}$, 13 (72%) of 18 ears were improved and 5 ears (28%) were unchanged, no worsening being observed. As shown in Table II, without Coenzyme $Q_{10}$, 2 (25%) of 8 ears were improved and 6 ears (75%) were unchanged, no worsening being observed. From the results, it is apparent that Coenzyme $Q_{10}$ is effective as a medicament for treating impaired hearing.

| Case | Sex | Age | Original disease | SM | KM | KDM | GM | Total amount | Treatment | Period of administration of Coenzyme $Q_{10}$ | Drug used together | | (Total threshold value before the treatment)-(Total threshold value after the treament) | Judgement |
|---|---|---|---|---|---|---|---|---|---|---|---|---|---|---|
| 1 | Male | 38 | Pulmonary | ○ | ◎ | | | SM 96g / KM 18g | Discontinued | 1.0 month | None | Right ear / Left ear | 25− 0=25 / 45−20=25 | Unchanged / Unchanged |
| 2 | Male | 34 | Pulmonary | ◎ | | | | SM 50g | Discontinued | 0.5 month | Vitamin B complex | Right ear / Left ear | 65−15=40 / 110−40=70 | Improved / Improved |
| 3 | Male | 48 | Pulmonary | ◎ | ◎ | | | SM 43g / KM 7g | Continued | 0.5 month | Horse chestnut seed extract | Right ear / Left ear | 95−70=25 / 150−115=35 | Unchanged / Improved |
| 4 | Female | 48 | Tuberculous peritonitis | ◎ | | ◎ | | SM 82g / KDM 2.2g | Discontinued | 1.5 month | Vitamin B complex | Right ear / Left ear | 110−50=60 / 95−50=45 | Improved / Improved |
| 5 | Female | 49 | Bronchopneiumonia | ◎ | ◎ | ◎ | ◎ | SM 4g / KM 7g / KDM 2.8g / GM 1.08g | Continued | 1.0 month | Horse chestnut seed extract | Right ear / Left ear | 195−155=40 / 230−180=50 | Improved / Improved |
| 6 | Female | 54 | Spiral caries | ○ | | | | SM | Discontinued | 4.0 months | Horse chestnut seed extract | Right ear / Left ear | 460−390=70 / 260−220=40 | Improved / Improved |
| 7 | Male | 48 | Pulmonary | ◎ | | | | SM 7g | Continued | 0.5 month | None | Right ear / Left ear | 190−165=25 / 155−140=15 | Unchanged / Unchanged |
| 8 | Female | 40 | Pneumonia | | | ◎ | | KDM 1.6g | Discontinued | 1.0 month | Glycyrrhizin preparation | Right ear / Left ear | 140−35=105 / 110−0=110 | Improved / Improved |
| 9 | Male | 70 | Dyelitis | | ◎ | | | KM 50g | Discontinued | 0.5 month | None | Right ear / Left ear | 370−335=35 / 445−290=155 | Improved / Improved |

| Case Sex Age | Original disease | Antibiotic Total amount | Antibiotic Treatment | Medicament for deafness | Period of use of medicament for deafness | (Total threshold) value before the treatment)-(Total threshold value after the treatment) | | Judgement |
|---|---|---|---|---|---|---|---|---|
| 1 Male 59 | Pleurisy | SM 20g | Discontinued | ATP preparation Betahistine preparation | 2.0 months | Right ear Left ear | 155−145=10 110− 95=15 | Unchanged Unchanged |
| 2 Male 36 | Pumonary Tuberculous | SM 32g | Continued | None | 3.0 months | Right ear Left ear | 40−15=25 35−20=15 | Unchanged Unchanged |
| 3 Female 46 | Tuberculous salpingitis | SM 96g | Discontinued | ATP preparation Betahistine preparation | 5.0 months | Right ear Left ear | 245−180=65 230−195=35 | Improved Improved |
| 4 Male 44 | Renal tuberculosis | SM 50g | Discontinued | Vitamin B complex Isoxsuprine preparation | 1.0 month | Right ear Left ear | 65−45=20 100−95= 5 | Unchanged Unchanged |

The followings are the examples of effective pharmaceutical preparations for the administration of the Coenzyme Q in the present invention, but the invention is not limited thereto.

| Example 1 Capsules | |
|---|---|
| Coenzyme $Q_{10}$ | 5 g |
| Microcrystalline cellulose | 80 g |
| Corn starch | 20 g |
| Lactose | 22 g |
| Polyvinylpyrrolidone | 3 g |
| Total | 130 g |

The above composition was shaped into granules in a usual manner and charged in gelatin hard capsules.

| Example 2 Powders: | |
|---|---|
| Coenzyme $Q_{10}$ | 50 g |
| Microcrystalline cellulose | 400 g |
| Corn starch | 1000 g |
| Total | 1000 g |

Coenzyme $Q_{10}$ was dissolved in acetone and the solution was adsorbed on the microcrystalline cellulose and dried. It was then mixed with the corn starch to obtain the powders in a usual manner.

| Example 3 Tablets: | |
|---|---|
| Coenzyme $Q_{10}$ | 5 g |
| Corn starch | 10 g |
| Refined white sugar | 20 g |
| Calcium carboxymethyl cellulose | 10 g |
| Microcrystalline cellulose (Avicel) | 40 g |
| Polyvinylpyrrolidone (K-30) | 5 g |
| Talc | 10 g |
| Total | 100 g |

Coenzyme $Q_{10}$ was dissolved in acetone and then the solution was adsorbed on the microcrystalline cellulose and dried. It was then mixed with the corn starch, refined white sugar and calcium carboxymethyl cellulose. Then, an aqueous solution of polyvinylpyrrolidone was added thereto as binder. The mixture was shaped into granules in a usual manner. The granules were mixed with talc as lubricant and then shaped into 100 mg tablets.

| Example 4 Injections: | |
|---|---|
| Coenzyme $Q_{10}$ | 10 g |
| Nikkol HCO-60 | 37 g |
| Sesame oil | 2 g |
| Sodium chloride | 9 g |
| Propylene glycol | 40 g |
| Phosphate buffer (0.1 M, pH 6.0) | 100 ml. |
| Distilled water | ad 1000 ml. |

Coenzyme $Q_{10}$, Nikkol HCO-60, sesame oil and a half of propylene glycol were mixed together and the mixture was heated to about 80° C and thereby dissolved. The distilled water wherein the phosphate buffer, sodium chloride and propylene glycol had been dissolved previously was heated to about 80° C and added to the former solution to obtain 1000 ml. of aqueous solution. The aqueous solution was charged in 2 ml. ampoules and the ampoules were closed by fusion and sterilized by heating.

EXAMPLE 5

Capsules were produced in the same way as Example 1, except for the substitution of Coenzyme $Q_9$ in Example 1 for Coenzyme $Q_{10}$.

EXAMPLE 6

An injectable solution was produced in the same way as Example 4, except for the substitution of Coenzyme $Q_9$ for Coenzyme $Q_{10}$.

What is claimed is:

1. A method for treating partially impaired hearing which comprises administering to a human suffering from partially impaired hearing a therapeutically effective amount of Coenzyme Q having the formula:

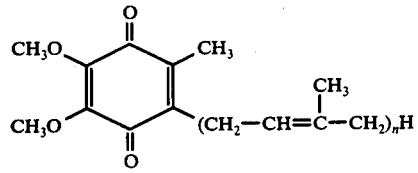

wherein n is an integer from 7 to 10.

2. A method as claimed in claim 1, wherein n is 10.

3. A method as claimed in claim 1, wherein the partially impaired hearing is partially impaired hearing caused by a side effect of a drug.

4. A method as claimed in claim 1, wherein said therapeutically effective amount is a daily dose of 10 - 200 mg of Coenzyme Q, administered orally.

5. A method as claimed in claim 1, wherein said therapeutically effective amount is a daily dose of 10 – 200 mg of Coenzyme Q, administered by injection.

6. A method as claimed in claim 1, wherein the partially impaired hearing is caused by continuous exposure to excessively loud noises, disease in the auditory pathways or in the auditory center, brain lesion, lesion of cortical brain substance, disease of the labyrinth, lesion of the auditory nerve or the central neutral pathways, disease of blood vessels of the inner ear, or side effects of drugs.

7. A method as claimed in claim 6 in which the therapeutically effective amount is an amount effective for decreasing the total hearing acuity threshold value for sounds of various frequencies in an audiometer test.

* * * * *